United States Patent
Heigl

(10) Patent No.: US 8,135,196 B2
(45) Date of Patent: Mar. 13, 2012

(54) OPERATING METHOD FOR A PIVOTAL POLY-PLANE IMAGING UNIT FOR IMAGING A MOVING EXAMINATION OBJECT

(75) Inventor: Benno Heigl, Coburg (DE)

(73) Assignee: Siemens Aktiengesellschaft, Munich (DE)

( * ) Notice: Subject to any disclaimer, the term of this patent is extended or adjusted under 35 U.S.C. 154(b) by 387 days.

(21) Appl. No.: 12/473,343

(22) Filed: May 28, 2009

(65) Prior Publication Data

US 2009/0297005 A1      Dec. 3, 2009

(30) Foreign Application Priority Data

May 30, 2008    (DE) .................. 10 2008 026 035

(51) Int. Cl.
  *G06K 9/00* (2006.01)
  *H05G 1/64* (2006.01)
(52) U.S. Cl. .............. 382/130; 382/154; 378/98.12
(58) Field of Classification Search .......... 382/128–134, 382/154; 128/920–925; 600/407–414, 424–426, 600/300; 378/207, 4
  See application file for complete search history.

(56) References Cited

U.S. PATENT DOCUMENTS

| | | | | |
|---|---|---|---|---|
| 7,831,088 | B2 * | 11/2010 | Frakes et al. ................. | 382/154 |
| 2005/0203386 | A1 * | 9/2005 | Heigl et al. ................... | 600/427 |
| 2006/0210019 | A1 | 9/2006 | Rasche et al. | |
| 2006/0210147 | A1 * | 9/2006 | Sakaguchi .................... | 382/154 |
| 2008/0181367 | A1 * | 7/2008 | Heigl et al. ................... | 378/207 |
| 2009/0067568 | A1 * | 3/2009 | Hall et al. ....................... | 378/4 |
| 2009/0076369 | A1 * | 3/2009 | Mistretta ....................... | 600/407 |
| 2009/0268029 | A1 * | 10/2009 | Haussmann et al. .......... | 348/153 |
| 2010/0246778 | A1 * | 9/2010 | Heigl et al. .................... | 378/207 |

FOREIGN PATENT DOCUMENTS

| | | |
|---|---|---|
| DE | 102005027963 B3 | 12/2006 |
| DE | 102006028326 A1 | 1/2008 |
| WO | WO 9749065 A1 | 12/1997 |

OTHER PUBLICATIONS

Prümmer et al.; "Cardiac C-arm CT: Efficient Motion Correction for 4D-FBP", SPIE Medical Imaging Conference, San Diego, CA, USA, Oct. 29-Nov. 4, 2006; Others; 2006.
"MediGuide—Medical Guidance System"; Internet-Link; Others.
Internet-Link "Carto XP Electroanatomical Mapping System from Biosense Webster . . ."; Others.
Siemens AG, "Somatom Definition Faster than every beating heart", Internet-Link; Others.
Siemens AG, "Syngo DynaCT Cardiac", Internet-Link; Others.

(Continued)

Primary Examiner — Hoa Pham

(57) ABSTRACT

The invention relates to a pivotal poly-plane imaging unit having a first and a second imaging planes arranged relative to each other at an offset angle and recording projection images of an moving examination object at a fan angle $\beta$. First and second projection images are recorded in different relative positions at respective instants by pivoting the imaging planes at an angle at least $180°+\beta$. Characteristic structures in the first and second projection images are detected. The characteristic structures are segmented by a vectorial representation and triangulated to obtain a three-dimensional representation of the characteristic structures. Three-dimensional displacement vector fields are determined that indicate displacements of the three-dimensional representation of the characteristic structures relative to a reference instant. A three-dimensional image is reconstructed using the three-dimensional displacement vector fields to display a state of the moving examination object at the reference instant.

13 Claims, 3 Drawing Sheets

OTHER PUBLICATIONS

Siemens AG, "Respiratory Gating", Internet-Link; Others;.
Siemens AG, "Respiratory Triggering", Internet-Link; Others; 2007.
Blondel et al.,"Reconstruction of Coronary Arteries From a Single Rotational X-Ray Projection Sequence", IEEE Transactions on Medical Imaging, vol. 25, No. 5, May 2006; pp. 653-663; Magazine.
Movassaghi et al.; "4D coronary artery reconstruction based on retrospectively gated rotational angiography: first in-human results"; Medical Imaging 2007: Visualization and Image-Guided Procedures. Edited by Cleary, Kevin R.; Miga, Michael I., Proceedings of the SPIE, vol. 6509, pp. 65090P (2007).; Others.
Shechter et al.; "Temporal tracking of 3D coronary arteries in projection angiograms"; Medical Imaging 2002: Image Processing , SPIE Proceedings vol. 4684, pp. 612-623, Feb. 2002; Others.

* cited by examiner

OPERATING METHOD FOR A PIVOTAL POLY-PLANE IMAGING UNIT FOR IMAGING A MOVING EXAMINATION OBJECT

CROSS REFERENCE TO RELATED APPLICATIONS

This application claims priority of German application No. 10 2008 026 035.5 filed May 30, 2008, which is incorporated by reference herein in its entirety.

FIELD OF THE INVENTION

The present invention relates to an operating method for a pivotal poly-plane imaging unit for imaging a moving examination object, in particular to a method for imaging the heart by means of an angiography device, for which purpose a bi-plane C-arm device shall be used by way of example here, and to a corresponding computer program, to a data carrier on which this is stored, and to a pivotal poly-plane imaging unit for carrying out the operating method.

BACKGROUND OF THE INVENTION

The term "poly-plane imaging unit" shall hereinafter be taken to mean an imaging unit comprising not just one pivotal plane, but a plurality of pivotal planes, in particular two or three, for image recording.

This invention relates in particular to angiography systems as are used for interventional procedures, for example on the heart. Traditionally angiography systems produce simple X-ray projection images on which structures such as heart shadows, guide wires, catheters and contrast-medium filled catheters can be seen. Typically newer-design angiography devices comprise a C-shaped arm, on one end of which an X-ray source is attached and on the other end of which an associated X-ray detector is attached. The C-arm can pivot freely about a patient couch and thereby allows two-dimensional real time X-ray images (fluoroscopy images) of the patient to be recorded from a wide variety of viewing directions. Such angiography systems can therefore also produce CT-like 3D images by rotating the C-arm around the patient, and this is also called a C-arm CT.

To use computed tomography and other three-dimensional reconstruction methods, such as PET (Positron Emission Tomography), SPECT (Single Photon Emission Computed Tomography) or MR (Magnetic Resonance) it is necessary for the data required for the respective modality of the image capture, from which a volume data element is to be produced, to match a precisely defined state of the examination object. In reality this is not always the case however as with many examination objects breathing, heartbeat or peristalsis, for example, cause movements in the examination object. Such movements cause artifacts in the images produced which sometimes significantly restrict or even entirely prevent clinical use of these representations. This problem occurs particularly clearly in the case of continually moving examination objects, such as the heart for example.

While an attempt can be made to remedy this problem by reducing the recording time of the raw data by way of quicker rotational movements of the CT device or by using two CT devices, this approach is not suitable for current C-arm devices.

A reverse method for solving this problem lies in selecting input data which matches a precisely defined state of the examination object and, more precisely, subsequently by what is known as "gating" (for example only using input data corresponding to a cardiac phase measured by means of an ECG or by using breathing sensors) or during data acquisition by "triggering", i.e. data are only recorded if a signal, for example from an ECG or a breathing sensor, indicates that the examination object is in the desired state). However this requires long times for data acquisition, and this leads to problems in particular if contrast medium is used or if for example further movements have to be suppressed by holding one's breath. The use of this approach also assumes that the movement of the examination object is periodic, and this is not the case for example with a movement caused by a combination of breathing and heartbeat or by arrhythmias.

SUMMARY OF THE INVENTION

The object underlying the present invention is to provide an operating method for a pivotal poly-plane imaging unit for imaging a moving examination object, and to a corresponding computer program, optionally stored on a data carrier, whereby the drawbacks known from the prior art are rectified and improved measurement results, in particular heart and vessel representations, are possible during an intervention or operation on the examination object. A pivotal poly-plane imaging unit for carrying out the operating method shall also be created.

This object is achieved by an operating method, a computer program or computer program products, a data carrier on which the latter is stored, and a pivotal poly-plane imaging unit as claimed in the claims.

Advantageous developments of the invention are the subject matter of the subclaims.

In the inventive operating method the imaging planes of the poly-plane imaging unit record the examination object in a first step in a single rotational pass respectively. In this case the term "rotational pass" is taken to mean that the two imaging planes are pivoted over an angular range of (at least) 180°+fan angle, with 50 to 500 images being recorded as a rule. The "fan angle" is the angle at which the X-ray source emits the X-rays and is usually about 20°.

The first imaging plane therefore records first projection images and the second imaging plane records second projection images. Optionally present additional recording planes also record additional projection images. The projection images are preferably recorded with a constant angular incrementation, i.e. the image is preferably recorded at previously defined angles or by passing through predefined angular elements or equidistant time segments. The recordings therefore preferably take place at equidistant instants $t_0, t_1, t_2, \ldots, t_n$. Alternatively it would be possible to record the projection images at a constant image rate, wherein the angular increments would then not be constant as the poly-plane imaging unit first has to be accelerated at the start and decelerated at the end and therefore the intervals between two successive image recordings are not constant. In total the imaging planes are pivoted by an angle of (at least) 180°+fan angle β, with 50 to 500 images being recorded as a rule. It is important in this connection that the two image planes record in an overlapping manner such that no "gaps" result between them during recording. The examination object is therefore recorded from two sides, i.e. at two different angles, which differ by the offset angle.

In a second step characteristic structures, which may be determined for example by appropriate contrasts or contrast differences, are detected in the two projection images.

In a third step the characteristic structures in the two projection images are segmented by displaying them vectorially. The term "segmenting" means that structures, such as contours, for example, are analyzed and brought into a vectorial description. They can be identified as a result.

These characteristic structures are then triangulated in a fourth step in order to be able to convert them into a three-dimensional representation. The third and fourth steps do not necessarily have to be carried out successively; instead they may also be combined into a single step and be carried out together or simultaneously in order to smooth out inconsistencies for example.

In a fifth step three-dimensional displacement vector fields are then estimated from the characteristic structures that change over time. Each displacement vector field indicates the displacement of the three-dimensional representation of each point of a respective characteristic structure in this case and, more precisely, between the respective recording instant and a reference instant.

In a sixth step a three-dimensional reconstruction is then carried out, the three-dimensional displacement vector factors being used to be able to display the examination object in the state at the reference instant.

Therefore according to the invention outstanding representations of the examination object can be created in a very short time, it being possible to reduce the radiation dose and the quantity of contrast medium to be administered. Even more details, for example soft tissue in the vicinity of the characteristic structures, may also be depicted by the images recorded in one rotational pass. Furthermore, the inventive operating method is not dependent on the examination object moving periodically, instead any desired movements may be used. No ECG signal is required for a successful execution of the inventive operating method either.

It is preferred for the offset angle γ to be between 70 and 110°, preferably between 80 and 100°, an angle of 90° being particularly preferred as the precision of image generation is highest in the above-mentioned fourth step in this case.

Vessels (such as their outer contours), their center lines, or both, are preferably used as the characteristic structures. This allows particularly simple and efficient image generation, in particular if the examination object is the heart.

The reconstruction of the images can be made even more reliable if markers to calculate additional data points for determining the three-dimensional displacement vector fields are applied. This is particularly advantageous with reconstruction of the heart, it then being possible to apply the markers to the chest.

A bi-plane C-arm angiography system is preferably used as the medical X-ray system, which, in other words, comprises two imaging planes. Of course the inventive operating method can also be carried out analogously by using three or more imaging planes.

The administration of contrast medium which is usually necessary may advantageously be standardized and automated by means of an injector such that a contrast medium is injected so as to be synchronized with the start of the first step.

The inventive pivotal poly-plane imaging unit for imaging a moving examination object comprises (at least) first and second image imaging planes arranged relative to each other at an offset angle γ and recording at a fan angle β. A radiator and a detector are provided in each imaging plane and are arranged so as to oppose each other with respect to their swiveling axis and the examination object and are used to record first projection images and second projection images in different relative positions at respective, preferably equidistant, instants. The projection images are recorded by pivoting the imaging planes about an angle totaling at least 180°+β. The poly-plane imaging unit also comprises a control and evaluation system for its control. The control and evaluation system is configured in such a way that on the one hand it appropriately controls the radiator and detector for image recording and on the other hand evaluates the recorded data in accordance with one of the above-described methods.

BRIEF DESCRIPTION OF THE DRAWINGS

The invention will be described in more detail hereinafter with the aid of a preferred exemplary embodiment and with reference to the drawings, in which schematically.

DETAILED DESCRIPTION OF THE INVENTION

In its preferred embodiment for image recording the invention does not use a typically used mono-plane X-ray system, but a bi-plane C-arm X-ray system.

Figure 2:
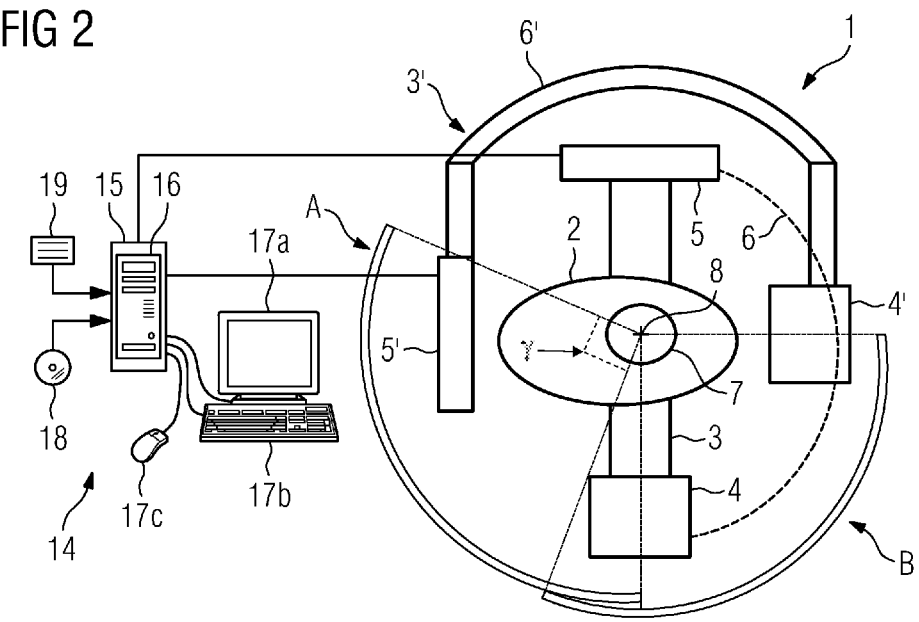
FIG. 2 shows a bi-plane C-arm unit configured according to the invention on which the inventive operating method can be executed.

FIG. 2 schematically shows a device 1 for producing a three-dimensional image data record of an examination object. The device 1 is a bi-plane X-ray tomograph, in particular a bi-plane 3D rotational angiography device. The examination object is the chest region, in particular the heart 7, of a patient 2.

In a first imaging plane A the device 1 comprises a recording unit 3 having an X-ray radiator 4 and an X-ray detector 5. The X-ray radiator 4 and the X-ray detector 5 are attached to the ends of what is known as a C-arm 6 (shown only in broken lines) so as to oppose each other and together with the latter define the first imaging plane A. The C-arm 6 is in turn substantially centrally mounted on a stand (not shown) so as to rotate about an isocentric shaft 8. The X-ray radiator 4 and the X-ray detector 5 can be rotated by pivoting the C-arm 6 in such a way that a central beam of the X-ray radiation emitted by the X-ray radiator 4 in the direction of the X-ray detector 5 can be pivoted within a recording plane perpendicular to the isocentric shaft 8 and with respect to the surrounding space in any desired projection angle (including what is known as the fan angle), the central beam always being aimed at the isocentric shaft 8.

In a second imaging plane B the device 1 also comprises a recording unit 3' having an X-ray radiator 4' and an X-ray detector 5'. The X-ray radiator 4' and the X-ray detector 5' are attached to the ends of a second C-arm 6' so as to oppose each other and together with the latter define the second imaging plane B which is arranged offset to the first imaging plane A by an offset angle γ of 90°.

The device 1 also comprises a patient's table (not shown) with a table top on which the patient 2 is situated during an examination such that the longitudinal axis of his body substantially aligns with the isocentric shaft 8 of the recording unit 3. For the examination the table top can be inserted into the opening of the C-arm 6 in such a way that the region of the body of the patient 7 to be examined comes to lie between the X-ray radiator 4 and the X-ray detector 5.

The device 1 also comprises a control and evaluation system 14. The control and evaluation system 14 comprises a data processing unit 15 in which, in addition to operating and control functions (not shown in more detail), a reading device for a computer program 19 stored on a data carrier 18, such as a CD or a USB stick, and an evaluation unit 16 for generating a three-dimensional (3D) image data record of the examined region of the body of the patient 2 is implemented. The control and evaluation system 14 also comprises input/output means, such as screen 17a, keyboard 17b, mouse 17c or the like for inputting control instructions and for displaying state variables, examination results, etc.

During the course of the method carried out by the device 1 digital image data are supplied to the evaluation unit 16 by the recording unit 3.

Figure 1:
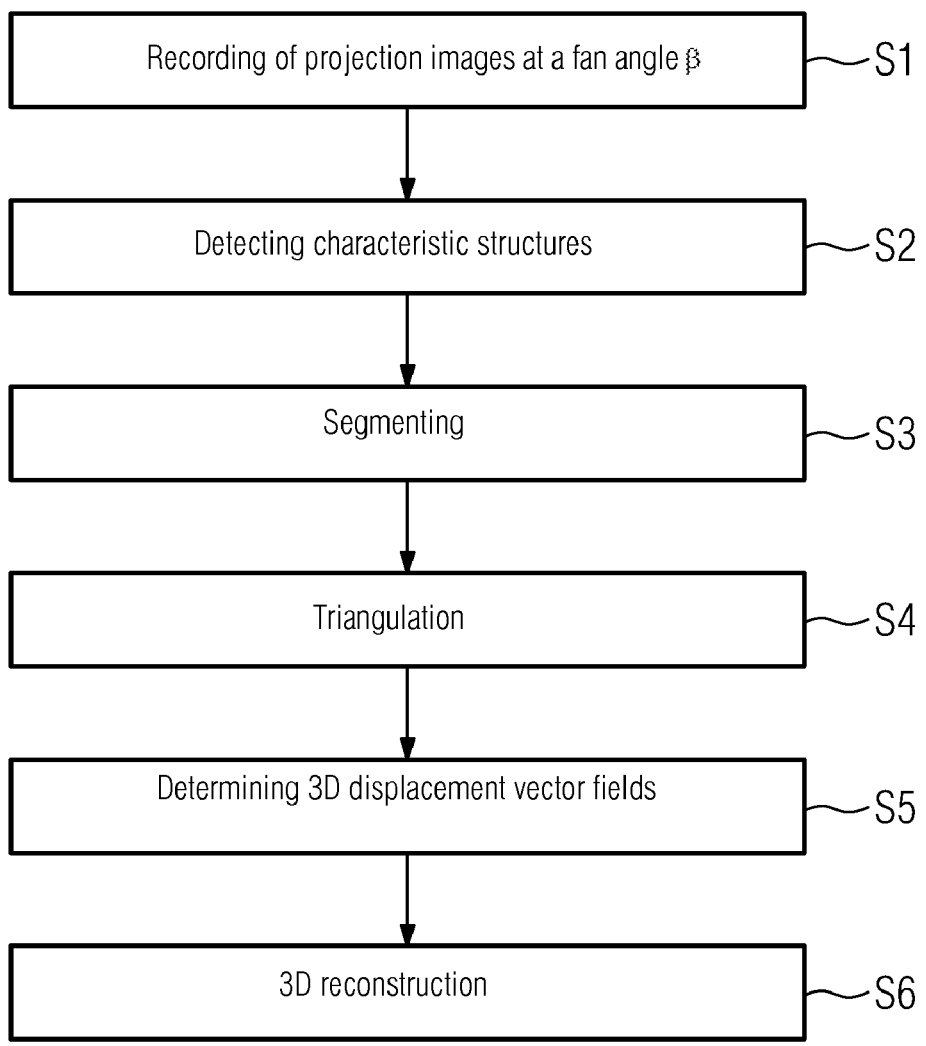
FIG. 1 shows a flow diagram which illustrates the basic progression of an inventive operating method for imaging a heart with the associated vessels.

For a 3D reconstruction it is basically necessary that projection images are obtained over an angular range of (at least) 180°+fan angle β, with 50 to 500 images being recorded as a rule. Hereinafter for simplification it will be assumed that the fan angle β is 20° and therefore an angular range of 200° has to be covered. This fan angle β can also assume other values, for example in the range of 0 to 40°, but in particular in the range of 10 to 30°. Both C-arms 6, 6' of the imaging planes A and B are arranged mutually offset by the offset angle γ, γ being assumed to be 90°, without limiting the generality. The two C-arms therefore start in initial positions offset by 90° (cf. FIG. 2). Once recording has started the two C-arms rotate in a first step S1 (cf. flow diagram of FIG. 1) over an angular range of 110°, i.e. the first C-arm 6 records projection images in the range from 0° to 110° while the second C-arm 6' records projection images in the range from 90° to 200°.

Figure 3:
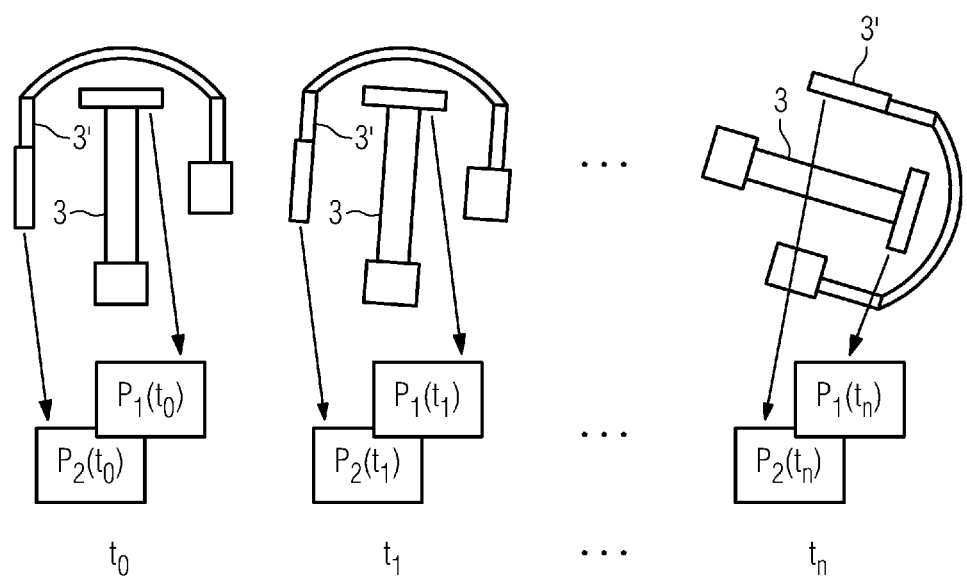
FIG. 3 shows different positions of the inventive bi-plane C-arm device during the course of a recording.

The two image recording systems therefore record mutually synchronized projection images ($P_1(t_i)$) and ($P_2(t_i)$) with a conventionally constant angle increment. In other words, projection images are recorded by the two image recording systems respectively at instants $t_i = t_0, t_1, t_2, \ldots, t_n$. The blood vessels and optionally also the chambers of the heart are rendered visible, or rendered more visible, by contrast medium. The number of images n is conventionally 50 to several hundred per image recording system. FIG. 3 shows the progression over time of the image recording of the image pairs $P_1(t_i)$ and $(P_2(t_i)$ and the associated positions of the image recording systems, the initial state of the image recording system being shown at instant $t_0$, and the end state (following a rotational pass) of the image recording systems being shown at instant $t_n$. Characteristic structures in the projection images are determined in a step S2. These are the blood vessels or what are known as the vessel trees in particular.

Figure 4:
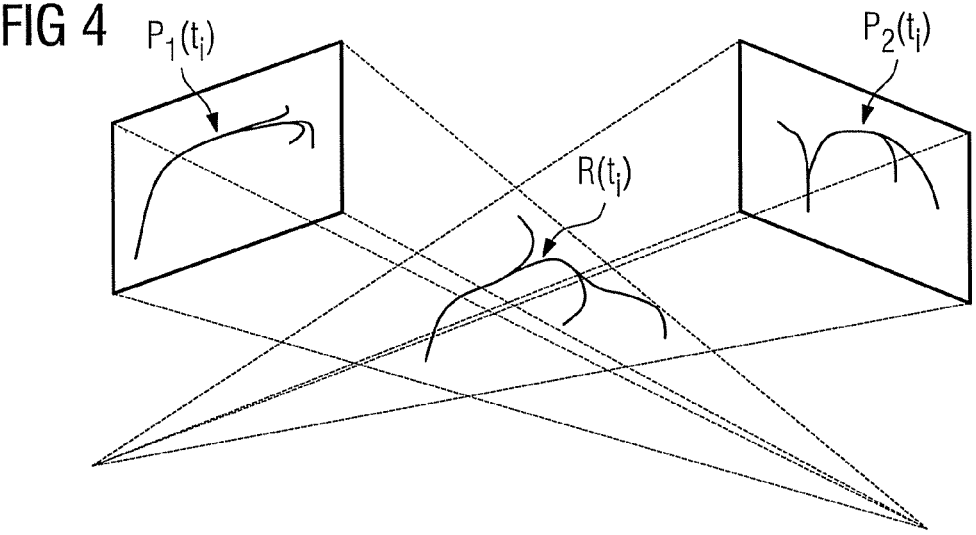
FIG. 4 shows a pair of projection images with respectively segmented vessel center lines and the three-dimensional vessel center line reconstructed therefrom by means of symbolic reconstruction.

What is referred to as a symbolic reconstruction of the center lines of the vessels is then carried out from two projections $P_1(t_i)$ and $(P_2(t_i)$ respectively, which have both been recorded at the same instant $t_i$ therefore. For this purpose firstly the vessel center lines of the blood vessels are segmented in the projection images in a step S3, i.e. the vessel center lines are analyzed and brought into a vectorial representation, so they may be identified. FIG. 4 shows this state schematically for the two projection images $P_1(t_i)$ and $(P_2(t_i)$. The three-dimensional vessel tree is then triangulated in a step S4 from the two-dimensional segmentations using known 3D geometry, and this is indicated by the three-dimensional vessel center line $R(t_i)$. A symbolic 3D reconstruction $R(t_i)$ of the vessel center lines is obtained as a result for each instant $t_i$ of image recording. Steps S3 and S4 do not necessarily have to be carried out successively, instead they can also be combined into a single step and be carried out together or simultaneously.

Figure 5:
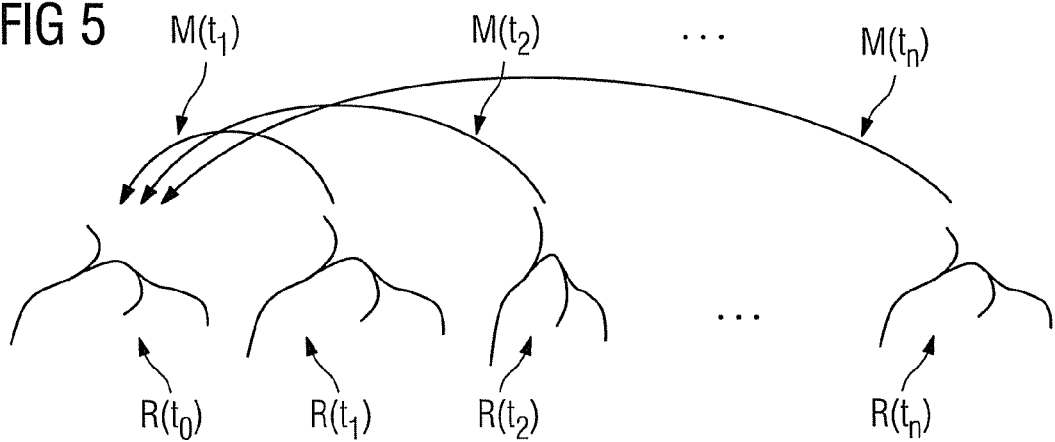
FIG. 5 shows a schematic view of vessel trees at different instants as well as their depiction on a vessel tree with respect to the reference instant.

Three-dimensional displacement vector fields $M(t_i)$ are then calculated in a step S5 from the reconstructed vessel center lines $R(t_i)$ at each instant $t_i$ for $i=2, 3, \ldots, n$, which indicate the displacement of each point on the vessel center lines at instant $t_i$ relative to instant to $t_0$. FIG. 5 firstly shows the displacement vector fields $M(t_1)$, $M(t_2)$, and $M(t_n)$ and secondly the deformations of the vessel trees $R(t_1)$, $R(t_2)$ $R(t_n)$ shown by these displacement vector fields at the respective instants against the instant ($t_0$) selected as the reference instant.

Figure 6:
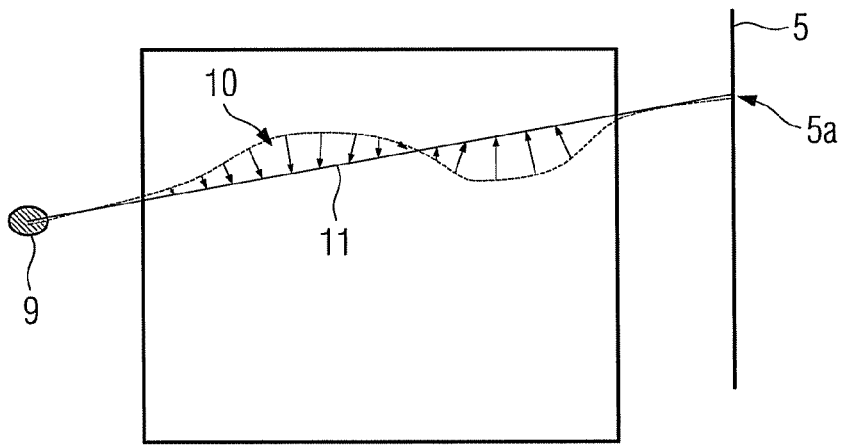
FIG. 6 shows a schematic view of the projection of an X-ray taking into account the nt vector field and ignoring same.

A movement-compensated 3D reconstruction then takes place in step S6, and this is also called movement-compensated computed tomography. For this purpose a three-dimensional volume data record is calculated from all input images for the instant $t_0$ by means of computed tomography. When settling each individual projection image, which was recorded at instant $t_i$, the movement vector fields $M(t_i)$ for instant $t_i$, calculated in step S5, are included in this connection such that the object state prevailing at instant $t_0$ is reproduced. FIG. 6 shows for the central layer of the 3D volume and an image recorded at time $t_i$ how a deformation caused by the movement of the heart is compensated by application of the displacement vector fields $M(t_i)$ during back projection of a line integral observed on an element 5a of a detector 5. By way of example the arrows designate individual vectors from a displacement vector field $M(t_i)$, which re-correct an apparently distorted, bent "line of observation" of the X-ray to a straight one again.

In the above-described embodiment the reference instant $t_0$ has been selected as the start of the recording. Of course any other desired instant $t_i$ may also be chosen as the reference instant. What is critical in this case is that ultimately an optimally good image of the heart with the vessels that surround it, and optionally of the soft tissue that is also of interest in the vicinity of the heart, is produced. It should be noted in this connection that, by way of example, a different choice of reference instant or repeated computed tomography can be carried out with the same images of a single rotational pass. In other words, changes of this kind or additional measures take place retrospectively and not after carrying out a new rotational pass.

It should be noted that, in addition to heart imaging, the inventive method can also be applied to any other desired, moving objects which comprise discrete characteristic structures which may be clearly identified in projection images and therefore allow the situation to be determined in a three-dimensional view from two projections that are perpendicular to each other or are almost perpendicular. Furthermore, additional data points for determining the three-dimensional movement vector fields may be calculated for example for the reconstruction of the heart by applying markers to the chest—which markers consist of parts of a specific shape, such as crosses, that are opaque to X-ray radiation, 10 to 20 such markers conventionally being used. These additional physical data points are intended in particular for extrapolation in regions outside the heart, but also for interpolation in regions which cannot otherwise be optimally represented. Overall an even more reliable reconstruction is made possible even in the regions which are further away from the blood vessels.

Advantages of the inventive method and the inventive imaging unit in connection with the corresponding computer program and the data carrier for its storage are:

C-arm units can be used, which owing to the known mechanical limitations have only a comparatively low angular velocity but can be used during an intervention or an operation on the heart.

The total time required for image recording can be minimized, making it possible to reduce radiation and the quantity of contrast medium to be administered. If, for example, two C-arms rotate synchronously at the same speed like a single C-arm for conventional rotational angiography, the image recording time is clearly reduced. If for example in a conventional method four rotational passes are required with a mono-plane C-arm device, a reduction by a factor of up to 8 is possible.

As "normal" computed tomography can be carried out using the recorded projection images in addition to a symbolic reconstruction, then not only can discrete structures such as blood vessels be displayed, but soft tissue in the vicinity of these discrete structures may also be depicted at the same time.

The movement of the examination object does not have to be periodic for the inventive method to be applied. Consequently mutually superimposed movements, such as breathing and heartbeat, may also be taken into account. Irregularities in the periodicity, as arrhythmias display for example, do not present any problems therefore. Furthermore, any one-off or non-periodic movements, such as swallowing, peristalsis, etc. are compensated.

It should be noted that the features of the invention described with reference to the illustrated embodiment, such as the exact sequence and the progression of individual steps, the dimension of the different angles and the type of images used for evaluation, may also be present in other embodiments even when something different is stated or they should not be considered for technical reasons per se.

The invention claimed is:

1. An operating method for imaging a moving examination object of a living body by a pivotal poly-plane imaging unit having a first and a second image recording units recording projection images of the moving examination object at a fan angle $\beta$, the method comprising:
    arranging the first and the second image recording units relative to each other by an offset angle $\gamma$ so that a first imaging plane of the first image recording unit is overlapped with a second imaging plane of the second image recording unit and no gaps between the first and the second imaging planes during the recording;
    mutually synchronized recording a first set and a second set of projection images of the moving examination object by the first and the second image recording units in a single rotational pass respectively in two different positions differing by the offset angle $\gamma$ at respective same instants, the first and the second image recording units being pivoted about an angle at least $180°+\beta$;
    detecting characteristic structures in the first set and the second set of projection images;
    segmenting the characteristic structures by a vectorial representation of the characteristic structures;
    triangulating the characteristic structures to obtain a three-dimensional representation of the characteristic structures;
    determining three-dimensional displacement vector fields indicating displacements of the three-dimensional representation of the characteristic structures relative to a reference instant; and
    reconstructing a three-dimensional image of the moving examination object using the three-dimensional displacement vector fields to display a state of the moving examination object at the reference instant.

2. The method as claimed in claim 1, wherein the offset angle $\gamma$ is between 70° to 110°.

3. The method as claimed in claim 2, wherein the offset angle $\gamma$ is between 80° to 100°.

4. The method as claimed in claim 1, wherein the characteristic structures are vessels of the moving examination object or center lines of the vessels.

5. The method as claimed in claim 1, wherein the moving examination object is a heart of the living body.

6. The method as claimed in claim 1, further comprising calculating additional data points for determining the three-dimensional displacement vector fields by applying markers in a vicinity of the moving examination object.

7. The method as claimed in claim 1, wherein the pivotal poly-plane imaging unit is an X-ray system.

8. The method as claimed in claim 7, wherein the pivotal poly-plane imaging unit is a C-arm angiography system.

9. The method as claimed in claim 1, further comprising synchronously injecting a contrast medium to the moving examination object when recording the first set and the second set of projection images.

10. The method as claimed in claim 1, wherein 50 to 500 projection images are recorded over the angle at least $180°+\beta$.

11. A computer program product executable on a control and evaluation unit of a pivotal poly-plane imaging unit having a first and a second image recording units recording projection images of a moving examination object at a fan angle $\beta$, the computer program product comprising:
    a computer program code that:
        arranges the first and the second image recording units relative to each other by an offset angle $\gamma$ so that a first imaging plane of the first image recording unit is overlapped with a second imaging plane of the second image recording unit and no gaps between the first and the second imaging planes during the recording;
        operates the pivotal poly-plane imaging unit to mutually synchronized record a first set and a second set of projection images of the moving examination object by the first and the second image recording units in a single rotational pass respectively in two different positions differing by the offset angle $\gamma$ at respective same instants, the first and the second image recording units being pivoted about an angle at least $180°+\beta$;
        detects characteristic structures in the first set and the second set of projection images;
        segments the characteristic structures by a vectorial representation of the characteristic structures;
        triangulates the characteristic structures to obtain a three-dimensional representation of the characteristic structures;
        determines three-dimensional displacement vector fields indicating displacements of the three-dimensional representation of the characteristic structures relative to a reference instant; and
        reconstructs a three-dimensional image of the moving examination object using the three-dimensional displacement vector fields to display a state of the moving examination object at the reference instant.

12. A pivotal poly-plane imaging unit for imaging a moving examination object, comprising:
    a first image recording unit having a first imaging plane that records a first set of projection images of the moving examination object in first different relative positions at respective instants in a single rotational pass;

a second image recording unit having a second imaging plane and arranged relative to the first image recording unit by an offset angle $\gamma$ so that the first imaging plane is overlapped with the second imaging plane and no gaps between the first and the second imaging planes during the recording, wherein the second image recording unit mutually synchronized records a second set of projection images of the moving examination object in second different relative positions differing with the first different relative positions by the offset angle $\gamma$ at the same respective instants in the single rotational pass, the first and the second recording units recording the projection images at a fan angle $\beta$ and pivoted about an angle at least $180°+\beta$;

a control and evaluation unit that:
    detects characteristic structures in the first set and the second set of projection images;
    segments the characteristic structures by a vectorial representation of the characteristic structures;
    triangulates the characteristic structures to obtain a three-dimensional representation of the characteristic structures;
    determines three-dimensional displacement vector fields indicating displacements of the three-dimensional representation of the characteristic structures relative to a reference instant; and
    reconstructs a three-dimensional image of the moving examination object using the three-dimensional displacement vector fields to display a state of the moving examination object at the reference instant.

13. The pivotal poly-plane imaging unit as claimed in claim 12, wherein the first and the second recording units each comprises a radiator and a detector oppose to each other with respect to the radiator and the detector's swiveling axis and the moving examination object.

* * * * *